(12) United States Patent
Khalil et al.

(10) Patent No.: US 6,635,491 B1
(45) Date of Patent: Oct. 21, 2003

(54) METHOD FOR NON-INVASIVELY DETERMINING THE CONCENTRATION OF AN ANALYTE BY COMPENSATING FOR THE EFFECT OF TISSUE HYDRATION

(75) Inventors: Omar S. Khalil, Libertyville, IL (US); Johannes Sake Kanger, JP Hengelo (NL); Rene' Alexander Bolt, DB Enschede (NL); Frits Frans Maria de Mul, CJ Almelo (NL)

(73) Assignee: Abbott Labortories, Abbott Park, IL (US)

( * ) Notice: Subject to any disclaimer, the term of this patent is extended or adjusted under 35 U.S.C. 154(b) by 0 days.

(21) Appl. No.: 09/627,859

(22) Filed: Jul. 28, 2000

(51) Int. Cl.$^7$ .............................................. G01N 33/00
(52) U.S. Cl. ......................... 436/95; 436/164; 436/171
(58) Field of Search ....................... 436/95, 164, 171; 422/55, 68.1, 82.05, 82.09

(56) References Cited

U.S. PATENT DOCUMENTS

| 4,223,680 | A | * | 9/1980 | Jöbsis | 600/324 |
| 4,655,225 | A | * | 4/1987 | Dähne et al. | 600/316 |
| 4,805,623 | A | * | 2/1989 | Jöbsis | 600/328 |
| 5,222,496 | A | * | 6/1993 | Clarke et al. | 600/316 |
| 5,284,139 | A | | 2/1994 | Khalil et al. | |
| 5,672,875 | A | * | 9/1997 | Block et al. | 250/343 |
| 5,725,480 | A | | 3/1998 | Oosta et al. | |
| 5,743,262 | A | * | 4/1998 | Lepper et al. | 128/633 |
| 5,755,226 | A | | 5/1998 | Carim et al. | |

FOREIGN PATENT DOCUMENTS

| WO | 98/03847 | 1/1998 |
| WO | 99/39631 | 8/1999 |
| WO | 99/55222 | 11/1999 |

OTHER PUBLICATIONS

Amerov et al. "Method and device for noninvasive blood glucose measurement", Proc. SPIE–Int. Soc. Opt. Eng., 1999, 3599 (Optical diagnostics of Biological Fluids !V), 33–42, Abstract (STN, L7, Answer 8).*

(List continued on next page.)

Primary Examiner—Jill Warden
Assistant Examiner—Yelena Gakh
(74) Attorney, Agent, or Firm—David L. Weinstein

(57) ABSTRACT

A method for determining the concentration of an analyte in tissues. The method involves compensating for a change in the value of an optical property of the tissues, such as, for example, the scattering coefficient, resulting from a change in the hydration status of the tissues. The method comprises the steps of:

(a) measuring at least one optical property of a tissue sample at at least one wavelength at an initial time;

(b) calculating the absorption coefficient and the scattering coefficient of the tissue sample at the initial time;

(c) repeating the measurement of the at least one optical property of the tissue sample at at least a later time at the at least one wavelength;

(d) calculating the absorption coefficient and scattering coefficient of the tissue sample at at least the later time;

(e) calculating the change in the value of the absorption coefficient at the at least one wavelength to indicate the change in the water content of the tissue sample and the change in the value of the scattering coefficient to indicate both the change in the water content of the tissue sample and the change in concentration of an analyte in the tissue sample;

(f) correcting the value of the scattering coefficient to account for the effect of the change in the water content of the tissue sample; and (g) calculating the concentration of the analyte by means of the corrected value of the scattering coefficient.

8 Claims, 2 Drawing Sheets

OTHER PUBLICATIONS

Amerov et al. "Method and device for noninvasive blood glucose measurement", Proc. SPIE–Int. Soc. Opt. Eng. (1999), 3599(Optical Diagnostics of Biological Fluids IV), 33–42, complete document.*

Heinemann et al. "Non–invasive continuous glucose monitoring i Type I diabetic patients with optical glucose sensors", Diabetologia, 1998, v. 41, pp. 8484–854.*

Qu et al. "Monte Carlo modeling studies of the effect of physiological factors and others analytes on the determination of glucose concentration in vivo by near infrared optical absorption . . . ", J. Biomed. Opt., 1997, v. 2, No. 3, pp. 319–325.*

O.S. Khalil, et al., U.S. application Ser. No. 09/080,470 filed May 18, 1998.

O.S. Khalil, et al., U.S. application Ser. No. 09/198,094 filed Nov. 23, 1998.

X. Wu, et al., U.S. application Ser. No. 09/302,207 filed Apr. 29, 1999.

O.S. Khalil, et al., U.S. application Ser. No. 09/366,084 filed Aug. 3, 1999.

O.S. Khalil, et al., U.S. application Ser. No. 09/566,415 filed May 8, 2000.

O.S. Khalil, et al., U.S. application Ser. No. 09/419,461 filed Oct. 15, 1999.

* cited by examiner

METHOD FOR NON-INVASIVELY DETERMINING THE CONCENTRATION OF AN ANALYTE BY COMPENSATING FOR THE EFFECT OF TISSUE HYDRATION

BACKGROUND OF THE INVENTION

1. Field of the Invention

This invention relates to the determination of the concentration of an analyte in a tissue non-invasively. More particularly, the invention relates to the determination of the concentration of an analyte in a tissue non-invasively by compensating for changes in the water content of the tissue resulting from a change in a disease condition or a change in a physiological condition.

2. Discussion of the Art

Optical monitoring of metabolites non-invasively is an important tool in clinical diagnostics. The ability to determine the concentration of an analyte or a disease state in a human subject without performing an invasive procedure has several advantages as compared with such determinations by invasive procedures. These advantages include, for example, ease of performing the test, reduction of pain, and decreased exposure to potential biohazards. The use of non-invasive procedures typically results in increased frequency of testing, increased accuracy in monitoring and control, and improved patient care. As used herein, a "non-invasive" technique (alternatively referred to herein as a "NI technique") is one that can be used without removing a sample from, or without inserting any instrument into, the tissues of the body. Non-invasive techniques typically involve irradiating a vascular region of the body with electromagnetic radiation and measuring the spectral information that results from absorption, scattering, and emission of light by the tissue.

Measurements in the 550–1300 nm region of the electromagnetic spectrum are commonly used in the art of non-invasive determinations. This spectral region is located between the visible bands characteristic of hemoglobin absorption and the infrared bands characteristic of water absorption. Electromagnetic radiation penetrates to a sufficient depth in the tissue to allow use thereof in a spectral measurement or a therapeutic procedure.

Determination of hemoglobin and hematocrit values non-invasively would offer a simple, biohazard-free, painless procedure suitable for use in blood donation centers. Non-invasive determinations of hemoglobin and hematocrit values are useful for the diagnosis of anemia in infants and mothers, because these determinations avoid the pain associated with pediatric blood sampling. Non-invasive determination of hematocrit values can yield important diagnostic information for patients undergoing dialysis. A low hematocrit value will indicate incomplete dialysis, while a rapid increase in the hematocrit value during dialysis indicates that the patient may faint due to a reduction in blood pressure.

An important application for non-invasive diagnostics is in the field of diagnosis and monitoring of diabetes. Diabetes mellitus is a chronic metabolic disorder characterized by an absolute or relative insulin deficiency, hyperglycemia, and glycosuria. If uncontrolled, diabetes can result in a variety of adverse clinical manifestations, such as, for example, retinopathy, atherosclerosis, microangiopathy, nephropathy, and neuropathy. In its advanced stages, diabetes can cause blindness, coma, and ultimately death. Accurate control of blood glucose level in the "normal range", 60–120 mg/dL, is necessary for diabetics to avoid or reduce complications resulting from hypoglycemia and hyperglycemia. As used herein, "blood glucose level" means the concentration of glucose in venous or capillary blood (depending on the sample used), expressed in mg/dL or as mM (molar) concentration.

The near-infrared region of the electromagnetic spectrum contains portions of the hemoglobin and water absorption bands. These bands are several orders of magnitude more intense than are glucose overtone absorption bands. Thus, measurement of blood glucose level will be greatly affected by changes in hemoglobin absorption and water absorption.

U.S. Pat. Nos. 5,086,229; 5,324,979; and 5,237,178 describe non-invasive techniques for measuring blood glucose level. In these methods, a blood-containing body part is illuminated and light that is transmitted through or reflected from the body part is detected. The blood glucose level is calculated from the signals measured. These patents are silent with respect to the effect of change in the water content of the body on the signal measured.

U.S. Pat. Nos. 5,187,672; 5,122,974; 5,492, 5,492,118; 5,713,352; and 5,770,454 describe frequency-domain methods and apparatus for determination of the scattering coefficient of tissues and calculation of the concentration of analytes, but are silent with respect to the effect of changes in the water content of the body on the scattering signal measured.

U.S. Pat. No. 5,337,745 describes a pulsatile-based method for determining the concentrations of compounds in the blood stream.

Spatially resolved diffuse reflectance techniques, described in U.S. Pat. Nos. 5,551,422; 5,676,143; 5,492,118; 5,057,695, European Patent Application EP 0810429, are silent with respect to the effect of change in the water content of the body on determination of blood glucose level from scattering data. Thus, two identical values of blood glucose level at different water contents of the body will result in different values for the scattering coefficient of the tissue.

Water is the major component of the human body. It is estimated that tissues contain from about 70% to about 80% water. Change in the water content of the tissue results in a large variability in the optical properties of the tissue. According to Wilson et al., the change in the scattering coefficient resulting from an increase of 5 mM (90 mg/dL) in blood glucose level is equivalent to the change in the scattering coefficient resulting from a 1% increase in the water content of the tissue. This change in scattering coefficient is also equivalent to the effect of a 0.5° C. decrease in temperature (J. Qu, B. Wilson, Journal of Biomedical Optics, 2(3), July 1997, pp. 319–325).

Although a variety of spectroscopic techniques are disclosed in the art, there is still no commercially available device that provides blood glucose level measurements non-invasively with an accuracy that is comparable to that of invasive methods. Thus, there is a continuing need for improved apparatus and methods for non-invasive determinations that are unaffected by variations in physiological conditions of tissues, such as water content, temperature, and perfusion. There is also a need for reagent-free, painless methods and devices for measuring blood glucose levels in diabetic patients.

SUMMARY OF THE INVENTION

This invention provides a method for determining the concentration of an analyte in tissue. The method involves compensating for a change in the value of an optical property of the tissue, such as, for example, the scattering coefficient, resulting from a change in the hydration status of the tissue. The method comprises the steps of:

(a) measuring at least one optical property of a tissue sample at at least one wavelength at an initial time;

(b) calculating the absorption coefficient and the scattering coefficient of the tissue sample at the initial time;

(c) repeating the measurement of the at least one optical property of the tissue sample at at least a later time at the at least one wavelength;

(d) calculating the absorption coefficient and the scattering coefficient of the tissue sample at at least the later time;

(e) calculating the change in the value of the absorption coefficient at the at least one wavelength to indicate the change in the water content of the tissue sample and the change in the value of the scattering coefficient to indicate both the change in the water content of the tissue sample and the change in concentration of an analyte in the tissue sample;

(f) correcting the value of the scattering coefficient to account for the effect of the change in the water content of the tissue sample; and (g) calculating the concentration of the analyte by means of the corrected value of the scattering coefficient.

Wavelengths at which the absorption coefficient is determined correspond to wavelengths of maximum or optimal absorption of a compound that is found in the tissue sample and that has a substantially high absorptivity. The absorption wavelengths of hemoglobin are preferred for such measurement. Hemoglobin has strong absorption bands in the near-infrared region of the electromagnetic spectrum, i.e., between 550 nm and 1100 nm. Also, hemoglobin is a compound that occurs naturally in the human body.

Alternatively, wavelengths at which the absorption coefficient is determined can correspond to wavelengths of maximum or optimal absorption of a compound that is found in the tissue sample, the compound being present in a substantially high concentration in the tissue, even though the compound may have low absorptivity.

The wavelengths at which the scattering coefficients are determined are selected to be the same wavelengths or close to the wavelengths at which the absorption coefficients are determined. This selection will assure that the absorption coefficients and the scattering coefficients are determined at the same depth in the tissue sample.

DETAILED DESCRIPTION

Figure 1:
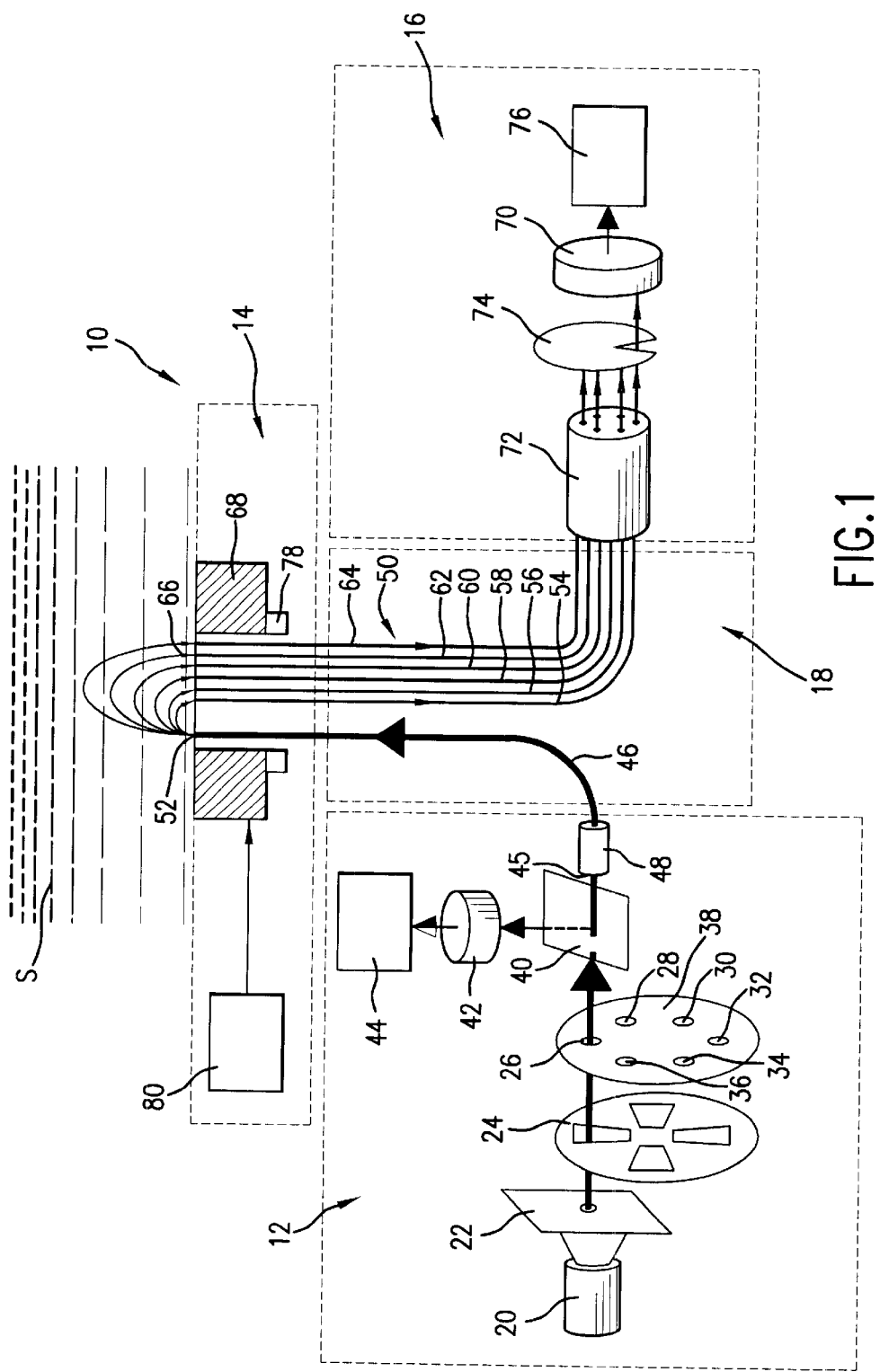
FIG. 1 is a schematic diagram illustrating an optical system that can be used to carry out the method of this invention.

As used herein, the expression "tissue sample" includes, but is not limited to, a sample of intact or excised human tissue, such as, for example, a sample of intact or excised human skin, or a human body part. The expression "tissue optics" refers to the study of light propagation in biological tissues. The expression "optical property" refers to one of the absorption, scattering, emission, reflectance, and depolarization properties of a tissue sample. The term "hematocrit" means the volume fraction of red cells in blood.

The expression "optical parameter" refers to a parameter that describes and defines an optical property of a medium and its components. Examples of optical parameters include, but are not limited to, absorption coefficient, scattering coefficient, anisotropy factor, transport optical mean free path, and the extinction coefficient of an analyte. The expression "scattering media" refers to media that scatter light. Scattering media may contain components that absorb light. The expression "absorption coefficient" (i.e., $\mu_a$) refers to the probability of light absorption per unit path length. The expression "scattering coefficient" (i.e., $\mu_s$) refers to the probability of light scattering per unit path length. The expression "anisotropy factor" (i.e., g) refers to the average cosine of the scattering angle for a multiply scattered photon. The expression "reduced scattering coefficient" (i.e., $\mu'_s$) refers to the probability of equivalently isotropic (uniform in all directions) scattering per unit path length. The reduced scattering coefficient is related to the scattering coefficient $\mu_s$ and the anisotropy factor g by the relationship $\mu'_s = (1-g)\mu_s$.

The expressions "diffuse reflectance" and "reflectance" refer to measurement of the intensity of light that is re-emitted from a sample at all angles different from the direction of the incident light. The expressions "spatially resolved scattering" and "spatially resolved diffuse reflectance" refer to measurement of the intensity of light that is re-emitted from a sample at a set of discrete light collection sites at specific distances from a light introduction site. Alternatively, the foregoing expressions can refer to measurement of the intensity of light that is re-emitted at a given light collection site on the boundary of the sample, wherein the light re-emitted from the sample results from illuminating the sample at a set of discrete light introduction sites located on the same boundary of the sample at defined distances from the light collection site. In both instances, $\mu_a$ and $\mu'_s$ are calculated from the intensity of the re-emitted light as a function of distance from the introduced light, i.e., the intensity of the re-emitted light at a plurality of sampling distances. As used herein, the expression "sampling distance" means the distance from a light introduction site to a light collection site. The expressions "re-emitted light" and "reflected light" are used synonymously herein, as are the expressions "reflectance" and the "intensity of re-emitted light", unless otherwise indicated. The expression "frequency domain measurement" refers to a measurement of light involving the phase angle and/or the amplitude change of modulated incident light re-emitted from the sample and measured at a given distance from a light introduction site. The expression "beam of light" refers to a group of photons traveling together in nearly parallel trajectories toward a sample and striking the surface of the sample in a predefined area only. As a practical matter, the predefined area on the surface of a sample struck by a given beam of light is that area that is covered by an illuminating element, such as an optical fiber.

In one aspect, this invention provides a method for accurately determining the concentration of an analyte in tissue. The method accounts for the effect of a change in the water content of the tissue (tissue hydration status) on the value of an optical property of the tissue (e.g., light scattering) by measuring the change in the absorption of another component that is present in the tissue. It is preferred to measure the change in the absorption coefficient of a strongly absorbing compound, such as hemoglobin, and using the change in the absorption of that compound as an indication for the change in the water content of the tissue. The method of this invention can be applied by tracking the change in the absorption coefficient and the scattering coefficient of the tissue, resulting from a change in the volume of the tissue being optically examined. The change in the volume of the tissue is brought about by a change in its water content. In effect, the tissue "swells" when its water content increases and "shrinks" when its water content decreases.

The method comprises the steps of:

(a) measuring at least one optical property of a tissue sample at at least one wavelength at an initial time;

(b) calculating the absorption coefficient and the scattering coefficient of the tissue sample at the initial time;

(c) repeating the measurement of the at least one optical property of the tissue sample at at least a later time at the at least one wavelength;

(d) calculating the absorption coefficient and scattering coefficient of the tissue sample at at least the later time;

(e) calculating the change in the value of the absorption coefficient at the at least one wavelength to indicate the change in the water content of the tissue sample and the change in the value of the scattering coefficient to indicate both the change in the water content of the tissue sample and the change in concentration of an analyte in the tissue sample;

(f) correcting the value of the scattering coefficient to account for the effect of the change in the water content of the tissue sample; and (g) calculating the concentration of the analyte by means of the corrected value of the scattering coefficient.

The wavelengths at which the absorption coefficient is determined correspond to wavelengths of maximum or optimal absorption of a compound that is found in the tissue sample. This compound should have a substantially strong absorptivity (extinction coefficient). The compound preferred for use in the method of this invention is hemoglobin, which is a compound that occurs naturally in the human body. The spectral range of the measurement of the method of this invention is the wavelength range of from about 500 nm to about 1100 nm.

Alternatively, the compound can be present in a substantially high concentration and have a low extinction coefficient. Such a compound is water, which is a compound that occurs naturally in the human body. The preferred spectral range for the measurement is more preferably extended to the wavelength range of from about 500 nm to about 1500 nm.

The wavelengths at which the scattering coefficient is determined are selected to be the same wavelengths or close to the wavelengths at which the absorption coefficient is determined. This selection assures that the absorption coefficient and the scattering coefficient are determined at the same depth in the tissue sample.

When tissue samples, for example, samples of intact human skin, are irradiated at visible and near-infrared wavelengths of the electromagnetic spectrum, light is scattered, and the scattered light can be measured. When the average dimension (size) of the scattering entities (particles, such as cells mitochondria and fibers) is close to the magnitude of the wavelength of the radiation, the reduced scattering coefficient, $\mu'_s$, can be expressed using Mie theory as follows:

$$\mu'_s = 3.28\pi a^2 \rho (2\pi a n_{ex}/\lambda)^{0.37}(m-1)^{2.09} \quad (1)$$

where, $\rho$ represents volume density, i.e., the number of particles per unit volume; "a" represents the radius of the scattering particle (e.g., cells, mitochondria, or collagen fibrils); $n_{ex}$ represents the refractive index of the medium, which, in the case of the human body, is interstitial fluid (ISF); $m=(n_{in}/n_{ex})$, the ratio of the refractive index of the scattering particle $n_{in}$ to the refractive index of the medium $n_{ex}$; and $\lambda$ represents the wavelength of the light. See Graaff, et al., "Reduced light-scattering properties for mixtures of spherical particles: a simple approximation derived from Mie calculations", Applied Optics, 1992; Vol. 31: page 1370–1376.

Methods of determining $\mu'_s$ and $\mu_a$ are known in the art. These methods include the measurement of diffuse reflectance of skin tissue, measurement of spatially resolved diffuse reflectance of skin tissue, measurement of change in phase and modulation of a frequency modulated light beam as the light is re-emitted from skin tissue, and measurement of collimated transmission through skin tissue. For a given incident wavelength of light, $\mu'_s$ varies directly with either the size of the scattering particle, "a", or the refractive index ratio "m", as shown in Equation (1). Because the refractive index of the scattering particles, $n_{in}$, remains relatively constant, $\mu'_s$ is influenced primarily by volume density ($\rho$), the refractive index of the medium ($n_{ex}$), and the radius of the scattering particle ("a").

The electrolyte balance in a human body tightly controls the water content of the human body. Excess water is immediately extracted by the kidneys and is excreted as urine; a shortage of water is generally expressed as thirst. Perspiration, cutaneous water permeation, and respiration are other mechanisms for extracting water. However, certain physiological conditions or disease state conditions can lead to retention of excess water in human tissue. Edema resulting from kidney failure, pre-menstrual bloating, or uptake of some steroid hormones, such as cortisol, may cause retention of excess water in the human body. On the other hand, an individual may suffer from dehydration (decrease in water content of tissue and blood) for a variety of reasons. Excessive sweating, excessive menstrual bleeding, diarrhea, diseases, excessive physical exertion, or use of diuretics can lead to tissue dehydration and a temporary decrease in the water content of the tissue.

The value of $\rho$, which represents the number of particles per unit volume, e.g., the number of cells per unit volume of tissue, is constant over a short period of time. However, the value of $\rho$ may vary over a long period of time and with different physiological conditions. Changes in the water content of the tissue will affect the value of $\rho$, and hence, the value of the scattering coefficient as determined by Equation (1). Thus, if the water content of the tissue increases, the value of $\rho$ will decrease. Similarly, if the water content of the tissue decreases, the value of $\rho$ will increase. A change in the water content of the tissue will also change the value of the refractive index mismatch "m", because the concentration of the soluble analytes in the tissue is decreased. Thus, either a change in the number of cells in the observation volume, or a change in the refractive index of the interstitial fluid resulting from a change in the water content of the tissue, will lead to changes in the scattering coefficient of the tissue. This change in scattering coefficient will, in turn, affect the accuracy of the determination of concentration of analytes in the blood or the tissue when methods based on determination of the scattering coefficient are employed. U.S. Pat. Nos. 5,551,422; 5,676,143; 5,492,118; and 5,057,695 describe methods for the non-invasive determination of glucose that depend on measuring the scattering coefficient of the tissue. These patents, however, are silent with respect to the effect of change in the water content of the body on the determination of blood glucose level from scattering data. We have discovered that it is important to account for the effect that a change in the water content of the tissue has on the calculated value of the scattering coefficient before the calculated value of scattering coefficient is used to determine the concentration of a soluble analyte in human tissue, such as, for example, glucose.

Another analyte that is usually present at a constant concentration in the human body is hemoglobin. The concentration of hemoglobin varies over a narrow range for men and over another narrow, but lower and overlapping, range for women. Hemoglobin concentration decreases in the case of anemia, but is easily restored by proper therapy. An important hemodynamic parameter in the human body is the hematocrit. The hematocrit value (Hct %) is expressed as:

$$\text{Hct \%} = [\Sigma \text{ mean } V_{RBC}/(\Sigma \text{ mean } V_{RBC} + V_{plasma})] \times 100 \quad (2)$$

where

"mean $V_{RBC}$" represents the mean volume of the individual red blood cells in a volume of blood, "$\Sigma$ mean $V_{RBC}$" represents the total volume of red blood cells in a volume of blood, and "$V_{plasma}$" represents the volume of plasma in the same volume of blood. Thus, the hematocrit value is a measure of the volume fraction of red blood cells in blood.

Because of the rapidity of the equilibrium of the water content of the tissue and the water content of the blood, the hematocrit value is related to the water content of the tissue. The hematocrit value is constant over an extended period of time. However, the hematocrit value decreases in the case of anemia, internal bleeding due to ulcers, menstrual bleeding, and in post-operative bleeding. The hematocrit value increases when an individual moves to higher elevations or exerts a great amount of physical effort for a prolonged period of time, such as, for example, during mountain climbing or marathon running. Thus, the change in the value of hematocrit can be used as an indication of a change in the water content, a change in hemoglobin content, or both.

Hematocrit values for healthy men range from 40% to 50%. Hematocrit values for healthy women range from 32% to 45%. However, it is possible to observe hematocrit values of about 20% in the case of patients experiencing kidney failure, before dialysis. Hematocrit values increase up to 50% during dialysis. Excessive dialysis can lead to hematocrit values up to a level of 70%, which is dangerous. Above this level, the blood pressure drops suddenly and the patient will faint.

Hemoglobin has a broad electronic absorption band that extends between 600 nm and 900 nm. The absorption of hemoglobin is very strong at wavelengths between 400 nm and 650 nm. However, at wavelengths below 600 nm, melanin absorption (skin pigmentation) results in higher absorption values and inaccuracy in the measurement of hemoglobin. The ratio of the absorption of hemoglobin at a wavelength of 650 nm to the absorption of hemoglobin at a wavelength of 800 nm has been used as an indication for blood oxygen saturation. Water has weak absorption bands at wavelengths of 750 nm, 980 nm, and 1046 nm. Stronger absorption bands for water are located at wavelengths of 1300 nm and 1450 nm. Thus, wavelengths in the range of about 590 nm to about 1400 nm can be used for the determination of hemoglobin, water content of tissue, and hematocrit value. Some techniques for making these measurements are described in the prior art.

Several methods in the prior art describe spectral measurements and algorithms for the determination of glucose in the near infrared region of the electromagnetic spectrum (500–1400 nm). Some of these methods are based on transmission of light; others are based on scattering of light. Changes in the value of hematocrit or the water content of the tissue involve large changes in signal due to the high absorptivity of hemoglobin and the relatively high concentration of water in tissue and blood. A change in the optical signal measured in this spectral range resulting from a change in blood glucose level (or a change in concentration of other weakly absorbing analytes) will be greatly affected by the fluctuation in signal resulting from a change in the value of hematocrit or a change in the water content of the tissue. The optical signal (S) measured in this spectral range can be expressed as:

$$S = S_1(\text{tissue water content}) + S_2(\text{hemoglobin}) + S_3(\text{tissue structural factors}) + S_4(\text{tissue analytes}) \quad (3)$$

and, $$S_1 \geq S_2 \geq S_3 >> S_4 \quad (4)$$

The signal component $S_4$ (tissue analytes) represents the contribution of a change in the concentration of at least one analyte in the tissue, such as glucose, on the optical signal. The blood glucose level varies between 45 mg/dL to 450 mg/dL; this range encompasses a swing from a hypoglycemic condition to a hyperglycemic condition. The maximum change in glucose concentration is equal to 2.5 mM to 25 mM. At a water content of the body tissues of 70%, the concentration of water in the human body is approximately 38 Molar. Thus, a small percentage change in the hydration status of body tissues can lead to a change in signal that is much greater than that caused by a change in glucose concentration. For example, the change in the scattering coefficient resulting from a change in the water content of 1% is equal to a change of 5 mM (90 mg/dL) in blood glucose level. A change in the water content of 1% is equivalent to 560 mL for a 180-pound man or 420 mL for a 135-pound woman. Sweating, exercise, or consuming a large drink can easily achieve these changes in fluid volume.

It is important to account for the effect of changes in the water content of the tissue and the value of hematocrit on the signal before the calculation step that is used for the determination of the concentration of an analyte in the tissue. The effect of an increase in the water content of the tissue on the concentration of an analyte will be equivalent to diluting the concentration of the analyte in the tissue. Conversely, the effect of a decrease in the water content of the tissue on the concentration of an analyte will be equivalent to increasing the concentration of the analyte in the tissue. One way to mimic the effect of a change in the water content of the tissue and to compensate for such an effect involves the use of tissue-simulating phantoms. It is possible to change the water content of the phantom while keeping the concentration of the analyte constant. In this case the total volume of the solution will change. Alternatively, it is possible to change both the water content and the concentration of the analyte in the phantom while keeping the volume constant. A dye of known concentration can be used to mimic absorption of hemoglobin and allow measurement of the change in its absorbance as the water content or the concentration of the analyte is changed, while the volume remains constant.

The reduced scattering coefficient of the tissue is expressed as a function of both the changes in the water content of the tissue and in the concentration of the analyte, e.g., glucose, in the tissue. In the case of glucose, the scattering is expressed as follows:

$$\mu'_s = \mu^0_s (V_0/V)\{1 + c_1[G]\} \quad (5)$$

where
- $\mu^0_s$ represents the reduced scattering coefficient of the tissue at the initial hydration condition;
- $V_0$ represents the volume of the tissue at the initial hydration condition;
- $V$ represents the volume of the tissue at a hydration condition other than the initial condition;
- $c_1$ represents the fractional change in the reduced scattering coefficient as induced by glucose; and
- $[G]$ represents glucose concentration in the tissue.

The absorption coefficient of the tissue (which is primarily attributable to hemoglobin) can be expressed as:

$$\mu_a = \mu^0_a (V_0/V) \tag{6}$$

where,
- $\mu^0_a$ represents the absorption coefficient at the initial hydration condition,
- $\mu_a$ represents the absorption coefficient at a hydration condition other than the initial hydration condition, and
- $V_0$ and $V$ are as stated previously.

Thus, the change in the absorption coefficient $\Delta\mu_a$ and the reduced scattering coefficient $\Delta\mu'_s$ of human tissue as a result of a change in the water content of the tissue is expressed as a dilution effect. This dilution effect is equivalent to a change in volume of the tissue from an initial value $V_0$ to the value at the time of measurement $V$, and subsequent change of the reduced scattering coefficient from $\mu^0_s$ to $\mu'_s$ and the absorption coefficient from $\mu^0$ to $\mu_a$. The change in the absorption coefficient $\Delta\mu_a$ and the reduced scattering coefficient $\Delta\mu_s$ as a result of increase in the water content of the tissue can be expressed by the following equations:

$$\Delta\mu_a = \mu_a - \mu^0_a = \mu^0_a \{(V_0/V) - 1\} \tag{7}$$

$$\Delta\mu'_s = \mu'_s - \mu^0_s = \mu^0_s \{(V_0/V) - 1\} \tag{8}$$

The foregoing two equations can be solved simultaneously to determine the change in the reduced scattering coefficient due to a change in the water content of the tissue ($\Delta\mu'_s$). $\Delta\mu_s$ can be expressed in terms of the initial absorption coefficient ($\mu^0_a$), the initial reduced scattering coefficient ($\mu^0_s$) and the change in the absorption coefficient of a strongly absorbing chromophore ($\Delta\mu_a$) resulting from change in the water content of the tissue, as shown in Equation (9).

$$\Delta\mu'_s = (\mu^0_s/\mu^0_a)\Delta\mu_a \tag{9}$$

Thus, $\Delta\mu'_s$, which is the change in the reduced scattering coefficient as a result of the change in the water content of the tissue, i.e., a dilution effect, can be expressed in terms of the change in the absorption coefficient of a chromophore in the tissue and the initial values of the absorption and reduced scattering coefficients. A chromophore that can be selected to track changes in the water content of the tissue is hemoglobin, because of its strong absorption in the near infrared region of the electromagnetic spectrum.

By substituting Equations (7) and (8) into Equation (5) and rearranging the resultant equation to express the value of glucose concentration, it can be seen that:

$$[G] = \frac{1}{c_1}\left\{\frac{\mu'_s \mu^0_a}{\mu_a \mu^0_s} - 1\right\} \tag{10}$$

where $c_1$ is a coefficient that is determined by fitting measured glucose values to determined optical parameters in Equation (10).

By substituting the expression for $(\mu^0_s/\mu^0_a)$ from Equation (9) into Equation (10), it is possible to express the concentration of glucose in the tissue based on the change in the reduced scattering coefficient ($\Delta\mu'_s$) and the change in the absorption coefficient ($\Delta\mu_a$) of a strongly absorbing analyte. These changes are due to changes in the water content of the tissue and can be estimated from a series of time based measurements starting with initial values of $\mu^0_s$ and $\mu^0_a$. This relationship is shown in Equation (11).

$$[G] = \frac{1}{c_1}\left\{\frac{\Delta\mu'_s - \Delta\mu_a/c_2}{\mu^0_s + \Delta\mu_a/c_2}\right\} \tag{11}$$

where, $$c_2 \mu^0_a/\mu^0_s \tag{12}$$

$c_2$ is the ratio of the initial value of the absorption coefficient to initial value of the reduced scattering coefficient, at the measurement site of the tissue, at the time of the first measurement, i.e., before the change in the water content of the tissue. If a calibration procedure is performed at the time the first measurement is made, then $c_2$ is the ratio of the initial absorption coefficient $\mu^0_a$ to the initial reduced scattering coefficient $\mu^0_s$ at the time the measurement device is calibrated to a particular individual. In this case, the method of measurement can be used for tracking changes in the glycemic state of an individual over a long period of time.

EXAMPLES

The following non-limiting examples further illustrate the method of this invention.

Example 1

An example of an apparatus that can be used for the method of this invention is similar to that described in WO 99/59464 and U.S. application Ser. No. 09/080,470, filed May 18, 1998, assigned to the assignee of this application. Another example of an apparatus that can be used for the method of this invention is a similar apparatus described in U.S. Pat. Nos. 5,551,422; 5,676,143; 5,492,118; 5,057,695.

A temperature-controllable localized reflectance tissue photometer (TCLRTP) having the ability to control the temperature of the sample and vary the temperature of the sample within a small depth in the tissue was constructed. Details of the breadboard construction are described in WO 99/59464, incorporated herein by reference. Briefly, the apparatus 10 comprised a light source module 12, an optical probe module 14, and a signal detection module 16 as shown schematically in FIG. 1. These three modules were interconnected through a branched optical fiber bundle 18.

A 5-watt incandescent lamp 20 (Model L1041, Gilway Technical Lamp, Woburn, Mass.) powered by a constant voltage source (not shown) delivered nearly uniform light through a 2-mm diameter iris 22. Light was chopped at 150 Hz by an optical chopper 24 coupled to a lock-in amplifier (not shown). The beam was then defocused and passed through one of six 10-nm band pass filters 26, 28, 30, 32, 34, and 36 having individual central wavelengths at 590 nm, 650 nm, 750 nm, 800 nm, 900 nm, and 950 nm, respectively. The six band pass filters 26, 28, 30, 32, 34, and 36 were assembled in a filter wheel 38. A portion of the filtered light was diverted by a beam splitter 40 and focused onto a silicon photodiode 42 (Model S-2386-44K 6C, Hamamatsu, Hamamatsu-city, Japan) and a pre-amplifier 44 to generate a reference signal, which was used to correct for fluctuations in intensity of the lamp. The remainder of the filtered light beam was re-focused onto a first end of an illuminating element 46 housed at a source tip 48 of a fiber bundle 50. The illuminating element 46 was an optical fiber. The filters 26, 28, 30, 32, 34, and 36 were selected to cover selected wavelength bands in the spectra of hemoglobin and water.

A second end 52 of the illuminating element 46 and the first ends of six light collecting elements 54, 56, 58, 60, 62, and 64 were mounted in a common tip 66, situated at the center of a 2-cm diameter temperature-controlled disc 68.

The common tip 66 and the temperature-controlled disc 68 were parts of optical probe module 14. All of the elements 54, 56, 58, 60, 62, and 64 were optical fibers made of cladded silica, and they had a diameter of 400 $\mu$m (Fiberguide Industries, Stirling, N.J.). The distance from the center of each light collecting element 54, 56, 58, 60, 62, and 64 to the center of the end 52 of the illuminating element 46 defined the sampling distances $r_1$ through $r_6$ of this apparatus. These sampling distances are listed in Table 1.

TABLE 1

| Collection fiber | $r_1$ | $r_2$ | $r_3$ | $r_4$ | $r_5$ | $r_6$ |
|---|---|---|---|---|---|---|
| Sampling Distance, mm | 0.44 | 0.78 | 0.92 | 1.22 | 1.40 | 1.84 |

The light re-emitted from the skin "S" was collected by the light collecting elements 54, 56, 58, 60, 62, and 64 and transmitted to the detection module 16, where a single silicon photodiode 70, of the same type as the reference photodiode 42, measured the intensity of the light collected by the six light collecting elements 54, 56, 58, 60, 62, and 64. The second end of each light collecting element 54, 56, 58, 60, 62, and 64 was located in a detection tip 72. A rotating shutter 74 selected the optical signal from each light collecting element, one at a time, allowing each signal to be detected by the photodiode 70 and a pre-amplifier 76. A lock-in amplifier Model SR830 DSP, Stanford Research Systems, Sunnyvale, Calif., (not shown) coupled to the optical chopper 24 at the source module 12, processed the pre-amplified signals.

The optical signals measured can be used to calculate $\mu_s$ and $\mu_a$ at an initial time (i.e., the calibration point) and at times other than the initial time. The values of $\mu_s$ and $\mu_a$ thus calculated can be used to calculate the concentration of glucose in the tissue after compensation for the change in the absorption and the scattering coefficients.

These changes in the absorption coefficients and the scattering coefficients resulted from changes in body water content between the time of the two measurements.

Example 2

The apparatus described in Example 1 can be used to carry out the method of this invention to determine blood glucose level in diabetic patients undergoing kidney dialysis.

Because of nephritic disease, water is retained in the body, thereby resulting in an erroneous value of the scattering coefficient, and hence of the blood glucose level determined non-invasively. During dialysis the water content of the tissue, as well as the concentration of toxins, will be reduced. It is possible to monitor the change in the water content of the tissue by measuring the change in the hematocrit value. The change in the hematocrit value (the ratio of the volume of red blood cells to the volume of total cells and plasma) is due mainly to the volume of plasma, which is mainly water. A dialysis session usually consumes four hours, a period over which large swings in blood glucose level can take place, and it is inconvenient to carry out invasive finger stick sampling and measurements while the patient is undergoing dialysis. The method of this invention and an apparatus similar to that described in Example 1 can be used to track the change in blood glucose level of a diabetic patient undergoing kidney dialysis. The values of $\mu^0_s$ and $\mu^0_a$ can be determined either at the end of a dialysis procedure, when the patient is at his or her dry weight, or at the beginning of the dialysis procedure. The ratio $c_2 = \mu^0_a / \mu^0_s$ is calculated from Equation (12). The changes in the absorption coefficient and the scattering coefficient, $\Delta\mu_a$ and $\Delta\mu_s$, are determined during the dialysis procedure and can be used in accordance with Equation (11) to monitor the change in blood glucose level during the dialysis procedure. The coefficient $c_1$ is determined by a calibration procedure that involves a series of measurements of (1) blood glucose level carried out invasively and (2) optical signals obtained immediately after a dialysis is carried out. Phantom data previously obtained or same patient calibration data can also be included.

The method described in this example can also be used for the non-invasive determination of blood glucose level for of patients undergoing dehydration (loss of body water content) due to a disease or use of diuretics. The same method can be used in the case wherein the water content of the body is increasing because of a disease state. Also, bloating, edema, or water retention can result from steroid treatment or kidney failure.

Example 3

The method of this invention was exemplified by means of tissue-simulating phantoms. A phospholipid emulsion (Intralipid® suspension) to mimic tissue scattering, a dye to mimic a strong absorption of light by the body, various concentrations of water, and various concentrations of glucose were used to construct a set of tissue-simulating phantoms.

Solutions 1 through 9 were made in order to prepare a calibration grid. Data relating to solutions 1 through 9 are summarized in Table 2. The scattering and absorption coefficients of these solutions were determined by collimated transmission by means of a Shimadzu spectrophotometer. This set of tissue-simulating phantoms had various combinations of absorption coefficients (0, 1 and 2 $cm^{-1}$) and scattering coefficients (3, 7, and 10 $cm^{-1}$).

TABLE 2

(Solutions for preparing the calibration grid)

| Solution Number | Water (mL) | Evans Blue solution (mL) | Intralipid ® suspension (mL) | $\mu'_s$ ($cm^{-1}$) | $\mu_a$ ($cm^{-1}$) |
|---|---|---|---|---|---|
| 1 | 196.1 | 0 | 3.9 | 3 | 0 |
| 2 | 190.9 | 0 | 9.1 | 7 | 0 |
| 3 | 187 | 0 | 13.0 | 10 | 0 |
| 4 | 194.1 | 2 | 3.9 | 3 | 1 |
| 5 | 188.9 | 2 | 9.1 | 7 | 1 |
| 6 | 185 | 2 | 13.0 | 10 | 1 |
| 7 | 192.1 | 4 | 3.9 | 3 | 2 |
| 8 | 186.9 | 4 | 9.1 | 7 | 2 |
| 9 | 183 | 4 | 13.0 | 10 | 2 |

Each of the solutions was placed in a beaker. An optical probe similar to that descrived in Example 1 was used.

However, some of the distances between the optical fibers were changed. The three optical fibers were embedded in a Plexiglas® mold, and the mold was immersed below the surface of the liquid. Light at different wavelengths was introduced into each solution from a 400-micron quartz fiber and collected at two sampling distances (0.53 mm and 1.0 mm) from the light introduction fiber. The intensity of the reflected light at the 0.53 mm sampling distance was designated $R_1$, and the intensity of the reflected light at the 1.0 mm sampling distance was designated $R_2$. The value of $1/R_1$ was plotted against the value of $R_1/R_2$ for the nine solutions. By means of this grid, it was possible to transform reflectance values into absorbance coefficient and scattering coefficient values and vice versa. The light employed had a wavelength of 525 nm, and the signals collected were processed to obtain the absorption coefficient and the scattering coefficient in a manner similar to that descrived in WO 99/59464.

After the calibration grid was established, nine solutions (solutions 10 through 18) were prepared to cover three possible conditions, which are shown in Table 3. In the manner used for solutions 1 through 9, the value of $1/R_1$ was determined and plotted against the value of $R_1/R_2$ for the nine solutions (solutions 10 through 18). Three stock solutions—1.2 g/L Evans Blue, 10% Intralipid® suspension, and 1 M glucose solution—were used to make solutions 10 through 18.

In a first set of solutions (solutions 10, 11, and 12), a change in glucose concentration with no change in the absorption coefficient was simulated. These solutions were prepared by adding Intralipid® suspension (13 mL), Evans Blue stock solution (4 mL), and glucose stock solution in varying ratios to water. The total volume of the resultant solution was maintained constant at 200 mL, and the absorption coefficient was maintained constant at 2 cm$^{-1}$. Glucose concentration in the three solutions was 100, 500 and 1000 mM, respectively. The intensity of reflected light from the solutions was measured, and the absorption coefficient and the scattering coefficient were determined by means of the aforementioned calibration grid. $c_2$ was determined by means of Equation (12) and the values from solution 9. The concentration of glucose was determined by means of Equation (11). The plot of the concentration determined versus the actual concentration is shown as circles in FIG. 2.

In a second set of solutions (solutions 13, 14, and 15), three volumes of Intralipid® suspension were used. No glucose was added. Solution 13 contained Evans Blue solution (3.9 mL), water (183.5 mL), and Intralipid® suspension (12.6 mL); solution 14 contained Evans Blue solution (3.2 mL), water (186.4 mL), and Intralipid® suspension (10.4 mL); solution 15 contained Evans Blue solution (2.6 mL), water (188.9 mL), and Intralipid® suspension (8.5 mL). The total volume of each of solutions 13, 14 and 15 was 200 mL. The concentration of glucose was maintained constant (0 mM), and the concentrations of the scattering material and the dye were varied to mimic the effect of change in the water content only. The reflectance of each solution was measured, and the absorption coefficient and the scattering coefficient were determined by means of the aforementioned calibration grid. $c_2$ was determined by means of Equation (12) and the values from solution 9. The concentration of glucose was determined by means of Equation (11), and the plot of the determined concentration versus the actual concentration is shown as inverted triangles in FIG. 2. All predicted data points fell close to a glucose concentration of zero. These data points represent the case where there is a change in the hydration state (water content) of the tissues of the human body, while the glucose concentration remains constant. Although the amount of colored compound, Evans Blue, varied as a result of change in the water content of the solution, the scattering data and the concentration of glucose determined by the method of this invention was not affected.

Figure 2:
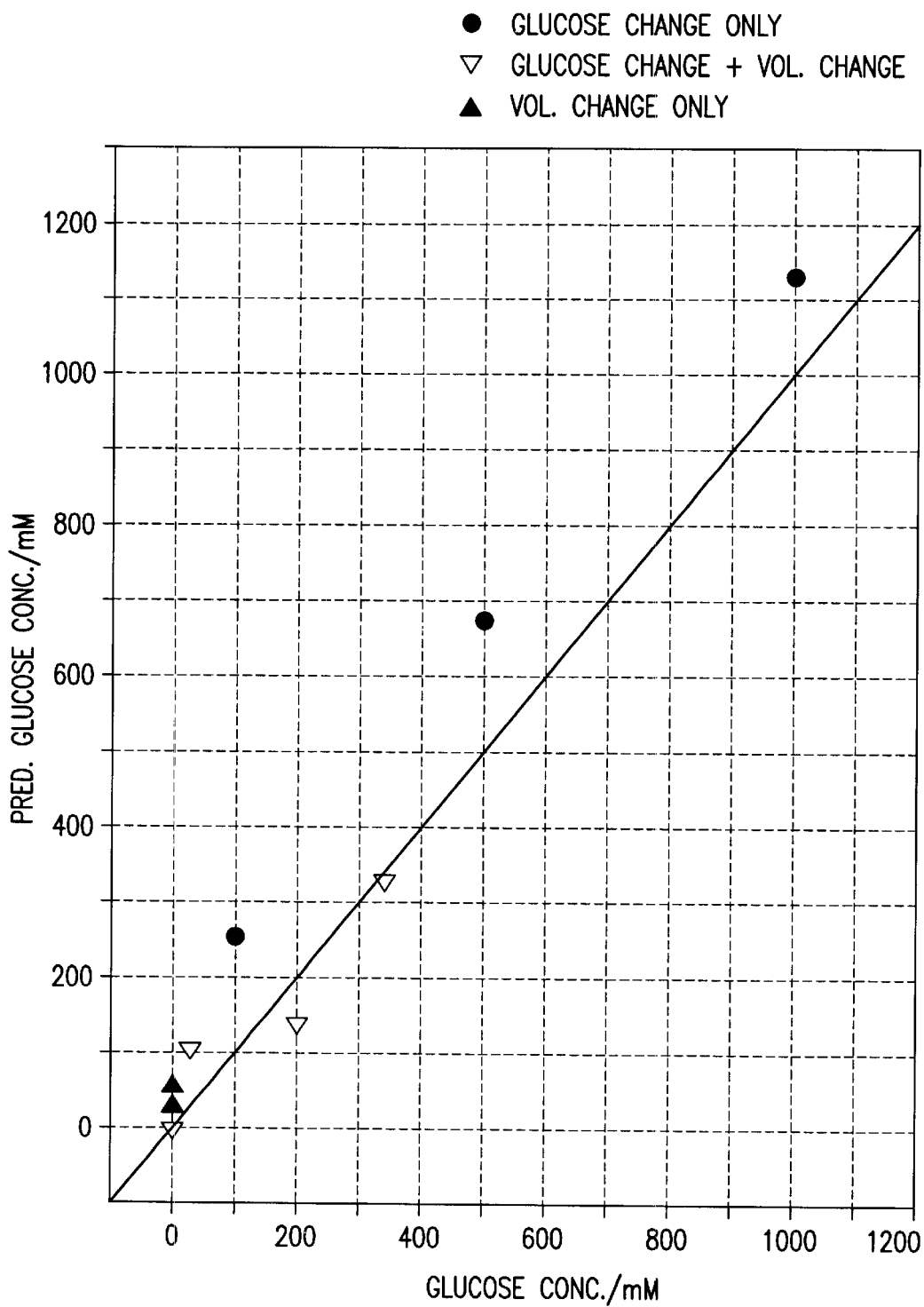
FIG. 2 is a graph illustrating the predicted glucose concentration when a suspension is diluted and the dilution effect is calculated from the absorption coefficient of an added dye (Evans Blue).

In a third set of solutions (solutions 16, 17 and 18), the volumes of Intralipid® suspension were varied in the same way as they were for solutions 13, 14, and 15. Solution 16 contained water (177.7 mL), glucose stock solution (5.8 mL, 1 M) to give 29 mM concentration of glucose, Evans Blue solution (3.9 mL), and Intralipid® suspension (12.6 ml). The total volume of the solution was 200 mL. Solution 17 contained water (146.6 mL), glucose stock solution (40 mL, 1 M) to give 200 mM concentration of glucose, Evans Blue solution (3.2 mL), and Intralipid® suspension (10.4 mL). The total volume of the solution was 200 mL. Solution 18 contained water (119.9 mL), glucose stock solution (69 mL, 1 M) to give 323 mM concentration of glucose, Evans Blue solution (2.6 mL), and Intralipid® suspension (8.5 mL). The total volume of the solution was 200 mL. The reflectance of each of the solutions was measured, and the absorption coefficient and the scattering coefficient were determined by means of the aforementioned calibration grid. The concentration of glucose was determined by means of Equation (11), and the plot of the determined concentration versus the actual concentration is shown as upright triangles in FIG. 2. These data points simulate the case where there is a change in the hydration state (water content) of the human body. Although the amount of colored compound, Evans Blue, varied as a result of changes in the water content of the solution, it was possible to use the values of $\Delta\mu_a$ to correct the scattering data for the effect of dilution due to change in the water content of the solution (which simulates the water content of the body). The concentration of glucose determined by the method of this invention, shown as upright triangles in FIG. 2, is close to the unity line. The closeness of the glucose concentrations predicted by Equation (11) to the actual values demonstrates the ability to determine glucose concentration even while the water content is changing, so long as compensation is made for the change in the absorption coefficient of a strongly absorbing chromophore. Data relating to solutions 10 through 18 are summarized in Table 3.

TABLE 3

(Test solutions)

| Solution number | Water (mL) | Glucose content | Evans Blue solution (mL) | Intralipid® suspension (mL) | Glucose (mM) | Comment |
| --- | --- | --- | --- | --- | --- | --- |
| 10 | 183 | 3.6 g | 4 | 13 | 100 | Glucose level varied. Volume |
| 11 | 183 | 18 g | 4 | 13 | 500 | remained |
| 12 | 183 | 36 g | 4 | 13 | 1000 | constant. |
| 13 | 183.5 | 0 | 3.9 | 12.6 | 0 | Water content varied. Glucose |
| 14 | 186.4 | 0 | 3.2 | 10.4 | 0 | level remained |
| 15 | 188.9 | 0 | 2.6 | 8.5 | 0 | constant. |
| 16 | 177.7 | 5.8 mL stock | 3.9 | 12.6 | 27 | Glucose level varied. Water content varied. |
| 17 | 146.4 | 40 mL stock | 3.2 | 10.4 | 200 | |
| 18 | 119.9 | 69 mL stock | 2.6 | 8.5 | 323 | |

In this example, the chromophore was Evans Blue dye. In the human body, the change in the absorption of hemoglobin can be used with Equations (11) and (12) to correct for the effect of change in hydration status on the blood glucose level, which is determined non-invasively.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for determining the concentration of an analyte in a sample of intact tissue, said method comprising the steps of:
   (a) measuring at least one optical property of said sample of intact tissue at at least one wavelength at an initial time, said at least one wavelength being in the range of from 550 nm to 1450 nm;
   (b) calculating the absorption coefficient and the reduced scattering coefficient of said sample of intact tissue at said initial time;
   (c) repeating the measurement of said at least one optical property of said sample of intact tissue at at least a later time at said at least one wavelength;
   (d) calculating the absorption coefficient and reduced scattering coefficient of said sample of intact tissue at at least said later time;
   (e) calculating the change in the value of the absorption coefficient at said at least one wavelength to indicate the change in the water content of said sample of intact tissue and the change in the value of the reduced scattering coefficient to indicate both the change in the water content of said sample of intact tissue and the change in concentration of an analyte in said sample of intact tissue;
   (f) correcting the value of the reduced scattering coefficient to account for the effect of the change in the water content of said sample of intact tissue; and
   (g) calculating the concentration of said analyte by means of the corrected value of the reduced scattering coefficient, wherein said light wavelengths at which said absorption coefficient is determined correspond to wavelengths of maximum absorption of a compound that is found in the sample of intact tissue.

2. The method of claim 1, wherein said compound has a substantially high absorptivity.

3. The method of claim 1, wherein said compound is hemoglobin.

4. The method of claim 1, wherein said spectral range of the measurement is between 550 nm and 1100 nm.

5. The method of claim 1, wherein the spectral range of the measurement is between about 500 nm and 1500 nm.

6. The method of claim 1, wherein said light wavelengths at which the reduced scattering coefficient is determined are selected close to the wavelengths at which the absorption coefficients are determined to assure that the light penetrates to the same depth in the sample of intact tissue.

7. The method of claim 1, wherein said analyte is glucose.

8. The method of claim 1, wherein said analyte is urea.

* * * * *

UNITED STATES PATENT AND TRADEMARK OFFICE
CERTIFICATE OF CORRECTION

PATENT NO.        : 6,635,491 B1                                        Page 1 of 1
APPLICATION NO.   : 09/627859
DATED             : October 21, 2003
INVENTOR(S)       : Omar S. Khalil, et al.

It is certified that error appears in the above-identified patent and that said Letters Patent is hereby corrected as shown below:

Col. 16, line 20
 Delete claim 5

Signed and Sealed this

Fourth Day of September, 2007

JON W. DUDAS
*Director of the United States Patent and Trademark Office*